(12) United States Patent
Davidson (10) Patent No.: US 11,975,900 B1
(45) Date of Patent: May 7, 2024

(54) EMERGENCY MEDICINE STORAGE AND DISPENSING DEVICE

(71) Applicant: Carey Davidson, Cave Creek, AZ (US)

(72) Inventor: Carey Davidson, Cave Creek, AZ (US)

( * ) Notice: Subject to any disclaimer, the term of this patent is extended or adjusted under 35 U.S.C. 154(b) by 0 days.

(21) Appl. No.: 18/388,662

(22) Filed: Nov. 10, 2023

Related U.S. Application Data (60) Provisional application No. 63/452,487, filed on Mar. 16, 2023.

(51) Int. Cl.
  *B65D 55/02* (2006.01)
  *B65D 85/00* (2006.01)
(52) U.S. Cl.
  CPC .............. *B65D 55/02* (2013.01); *B65D 85/00* (2013.01)
(58) Field of Classification Search
  CPC ..... B65D 55/02; B65D 85/00; B65D 2203/02
  USPC ...................................... 206/370, 438; 220/8
  See application file for complete search history.

(56) References Cited

U.S. PATENT DOCUMENTS

| | | | | |
|---|---|---|---|---|
| 3,802,555 A | * | 4/1974 | Grasty | A61B 50/30 206/505 |
| 5,732,821 A | * | 3/1998 | Stone | A61B 50/30 206/439 |
| 8,480,969 B2 | * | 7/2013 | Fukuzawa | A61B 5/14532 206/305 |

* cited by examiner

*Primary Examiner* — Bryon P Gehman
(74) *Attorney, Agent, or Firm* — Accelerate IP LLC (57) ABSTRACT

An emergency medicine storage and dispensing device includes a housing with a front section and a back section, a front panel with at least one pinhole, a lip extending from the sidewall, a cover securing the front panel, at least one cutout in the sidewall, a tray sliding into the housing through the at least one cutout, and a pin securing the tray in the housing. The front panel may be partially transparent and made from materials such as glass or plastic. The pin may be a breakaway pin with a thin breakaway section and a capturing section. The tray may have at least one slot holding at least one rapid chemical deployment system, such as an opioid overdose reversal medicine. The front section, back section, cover, and front panel may be substantially the same shape, such as triangular with chamfered ends.

16 Claims, 10 Drawing Sheets

SECTION A-A

*FIG. 16*

EMERGENCY MEDICINE STORAGE AND DISPENSING DEVICE

CROSS REFERENCE TO RELATED APPLICATION

This application claims benefit from currently U.S. Provisional Application No. 63/452,487 titled "Emergency Medicine Storage and Dispensing Device" and having a filing date of Mar. 16, 2023, all of which is incorporated by reference herein.

FIELD OF THE INVENTION

The present specification relates generally to devices for storing emergency medicine and more specifically a device that safely stores and quickly dispenses emergency medicine for drug overdose.

BACKGROUND OF THE INVENTION

Overdose is now a leading cause of death for those under 50 years of age. The "Opioid Epidemic" has been fueled in part with the in part with the introduction of a powerful synthetic opiate called fentanyl, which is often disguised as legitimate pharmaceuticals and candy, putting the general public at risk of an accidental death by an overdose. The number of overdose deaths have increased by more than 50% in the past few years and nearly 75% of them are related to opioids, including fentanyl, of which the vast majority of which are unintentional and preventable. So, individuals have developed medicine that works by blocking the effects of opiates on the central nervous system and restores breathing in the case of overdose of opioid/fentanyl poisoning. This type of medicine works by binding the opioid receptor to rapidly reverse the effects on the user of the opioid use. While, this type of medicine is often used by first responders, in hospitals and by individuals that are known to be at high risk of opioid overdose, however there are many cases of unintentional opioid use leading to an overdose and by the time the first responder arrives the individual has died due to lack of access to the antidote medication.

While efforts have been made reduce the flow legal and illicit opioids, and fentanyl lace pills, it has been largely been unsuccessful because of the high demand for mood altering drugs. The total economic cost of opioid use accounts for over $1.5 trillion in 2020 which is up by 37% from 2017. The numbers are increasing every year, for example, in 2020 the fatalities were 69,061 and in 2021 the fatalities were 80,926, and 112,00 in 2022 respectively. Sadly, even with increased public attention, the trend of unintentional overdose deaths are continuing to climb in all areas. The greatest tragedy that has come from this is the impact our families and communities that are suffering from inadvertently development of a substance use disorder, ongoing substance misuse and the needless and unintentional loss of life.

Opioid overdose can happen anywhere such as schools, workplaces, entertainment venues, public and private buildings, community centers, airports, libraries, anywhere. Most, if not all these places lack a dedicated and identifiable means to access lifesaving medicine which can prevent these unnecessary deaths. Therefore, there is a need for a unique and identifiable storage and dispensing system that can safely store multiple does of medicine that can rapidly deliver medicine in a crisis.

BRIEF SUMMARY OF THE INVENTION

Accordingly, the present invention relates to an emergency medicine storage and dispensing device. The emergency medicine storage and dispensing device can comprise a housing with a front section and a back section that are detachably coupled. The front section can include a front panel that can reside within the sidewall of the front section housing and encloses the front of the housing. The front panel can rest on a lip that can extend from at least a portion of the sidewall. A cover can secure the front panel between the lip and the front edge when the cover can be installed to the housing. The device can also include at least one cutout in the bottom side of the sidewall and a tray that is configured to slide into the housing through the cutout. A pin can secure the tray in the housing.

The front panel of the device can be at least partially transparent and can be manufactured from materials such as glass, plastic, plexiglass, polycarbonate, or laminated glass. The pin can be a break away pin having a thin break away section and a capturing section. The front panel can be compressed against the housing by at least one fastener. The back section of the device can have at least one wall mount. The tray can have at least one slot that holds at least one rapid chemical deployment system, such as an opioid overdose reversal medicine. The tray can also have a retainer that keeps the tray from being completely removed from the housing and a handle for easy operation. The back cover of the device can have at least one snap hook and at least one mounting boss.

The at least one fastener can be attached to the mounting boss. The front section can be coupled to the back section by the at least one second fastener, which can be a rivet, snap hook, or bolt. The front section, back section, cover, and front panel can be substantially the same shape, such as triangular with chamfered ends. This design allows for efficient storage and dispensing of emergency medicine, providing a reliable and accessible solution in emergency situations.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the. Absent such clear statements of intent to apply a "special" definition, it is the inventor's intent and desire that the simple, plain, and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112 (f). Thus, the use of the words "function," "means" or "step"

in the Detailed Description or Description of the Drawings or claims is not intended to somehow indicate a desire to invoke the special provisions of 35 U.S.C. § 112 (f), to define the invention. To the contrary, if the provisions of 35 U.S.C. § 112 (f) are sought to be invoked to define the inventions, the claims will specifically and expressly state the exact phrases "means for" or "step for" and will also recite the word "function" (i.e., will state "means for performing the function of . . . , without also reciting in such phrases any structure, material or act in support of the function. Thus, even when the claims recite a "means for performing the function of molding a . . . , step for performing the function of molding a . . . ," if the claims also recite any structure, material or acts in support of that means or step, or that perform the recited function, then it is the clear intention of the inventors not to invoke the provisions of 35 U.S.C. § 112 (f). Moreover, even if the provisions of 35 U.S.C. § 112 (f) are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

Additional features and advantages of the present specification will become apparent to those skilled in the art upon consideration of the following detailed description of the illustrative embodiment exemplifying the best mode of carrying out the invention as presently perceived.

BRIEF DESCRIPTION OF THE DRAWINGS

These and other features, aspects, and advantages of the present specification will become better understood with regard to the following description, appended claims, and accompanying drawings where:

Elements and acts in the figures are illustrated for simplicity and have not necessarily been rendered according to any particular sequence or embodiment.

DETAILED DESCRIPTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

Referring initially to FIGS. 1-8, an emergency medicine storage and dispensing device is shown generally at 10. The emergency medicine storage and dispensing device 10 can comprise a housing 12 comprising a front section 14 and a back section 16 detachably coupled to the front section. The front section 14 and the back section 16 when assembled define a front 15 having a front edge 21, a back 17 and a sidewall 19 about the periphery of the housing between the front and back of the housing 12. The front section 14 can have a cross section and the sidewall 19 that can have a bottom side 23. The front section 14 can comprise a front panel 20 which can reside within the sidewall 19 of the front section and encloses the front of the housing 12 wherein the front panel having at least one front panel pinhole 25. The front section 14 can have at least one cutout 34 in the bottom side 23 of the sidewall 19. The housing 12 including the front section 14 and back section 16 can be manufactured from such as, for example, sheet metal, aluminum, plastic, carbon fiber, stainless steel or the like.

Figure 14:
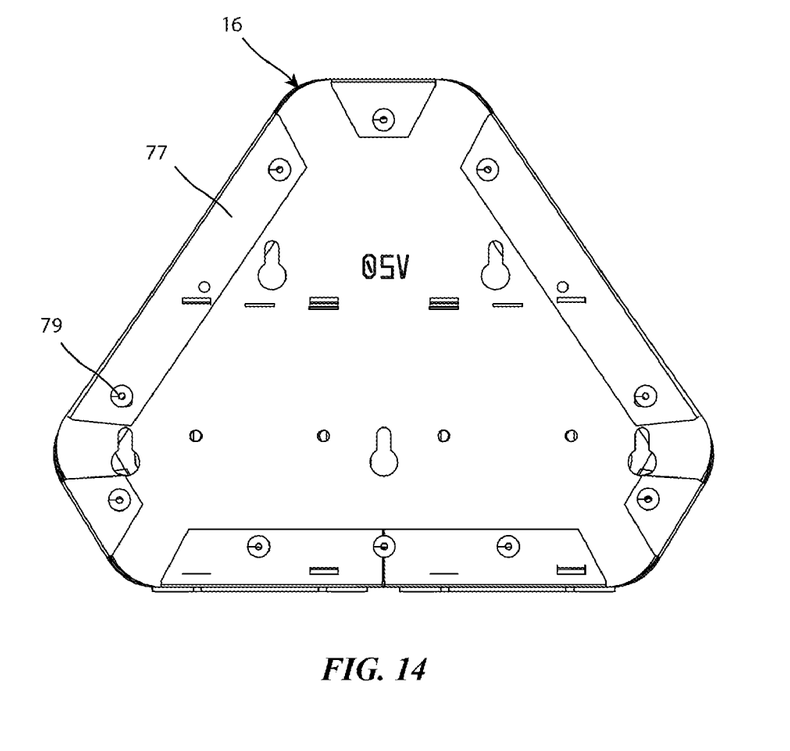
FIG. 14 is a back view of yet another embodiment of the emergency medicine storage and dispensing device in accordance to one, or more embodiments.

The back section 16 can have a back lip 56 that can partially extend from the back section toward the front section 14. The back section 16 can further comprise wall standoffs 52 that partially protrude from the back section 16 and have a wall mounting hole 54 which can allow the back cover to be attached to a wall by at least one fastener (not shown). The sidewall 19 can have at least one tab slot 40 positioned around its outer perimeter. The back lip 56 can have at least one snap hook 46 wherein the snap hook 46 can be removably coupled to the tab slots 40 on the housing 12 coupling the back section 16 to the font section 14. In other embodiments, the wall standoffs 52, snap hooks 46 and the back lip can be omitted, and the back section can be coupled to the front section by at least one back flange 77 and at least one back fastener 79 as shown in FIG. 14, wherein the back fasteners can be such as, for example, rivets, bolts, screws, or the like.

Figure 6:
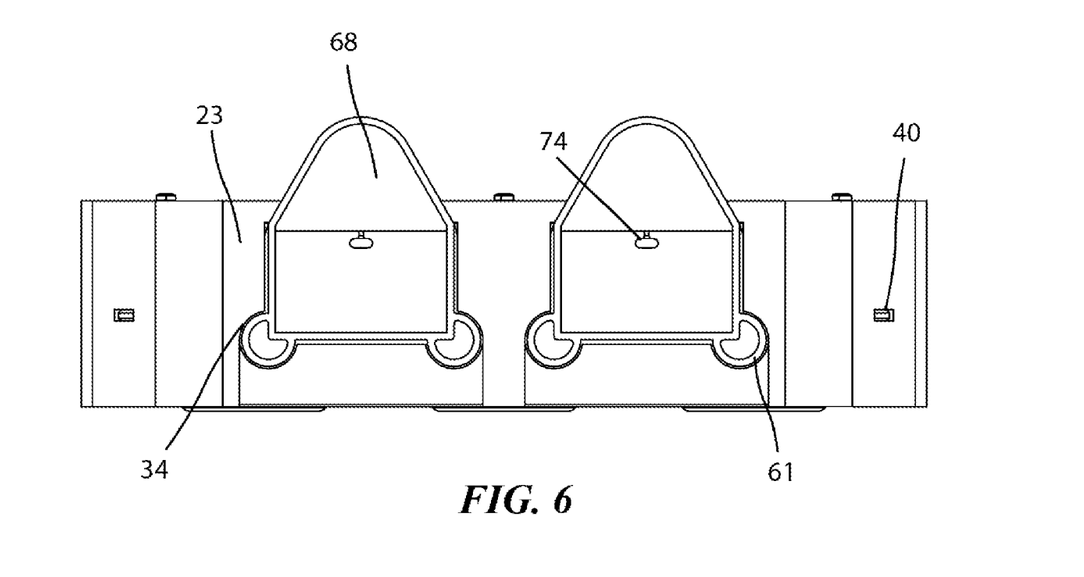
FIG. 6 is a bottom view of the emergency medicine storage and dispensing device in accordance to one, or more embodiments.
Figure 7:
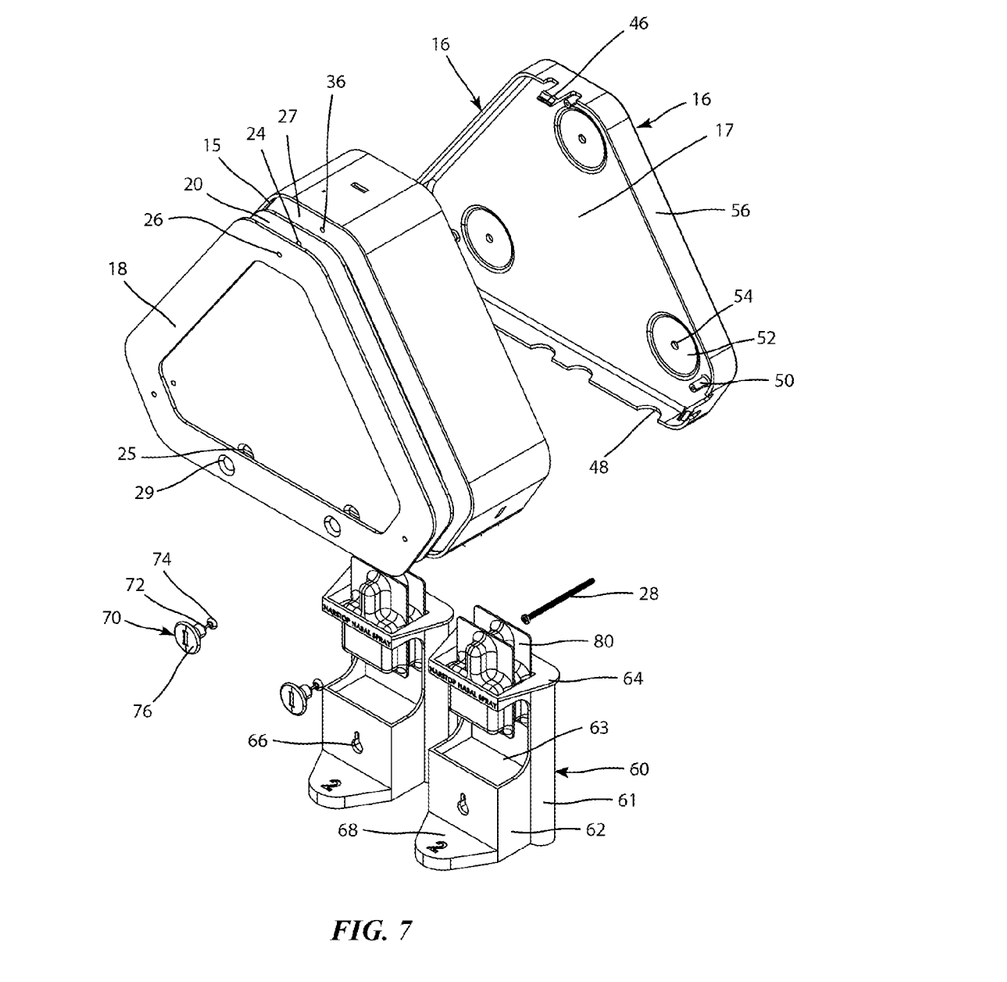
FIG. 7 is an exploded isometric view of the emergency medicine storage and dispensing device in accordance to one, or more embodiments.
Figure 8:
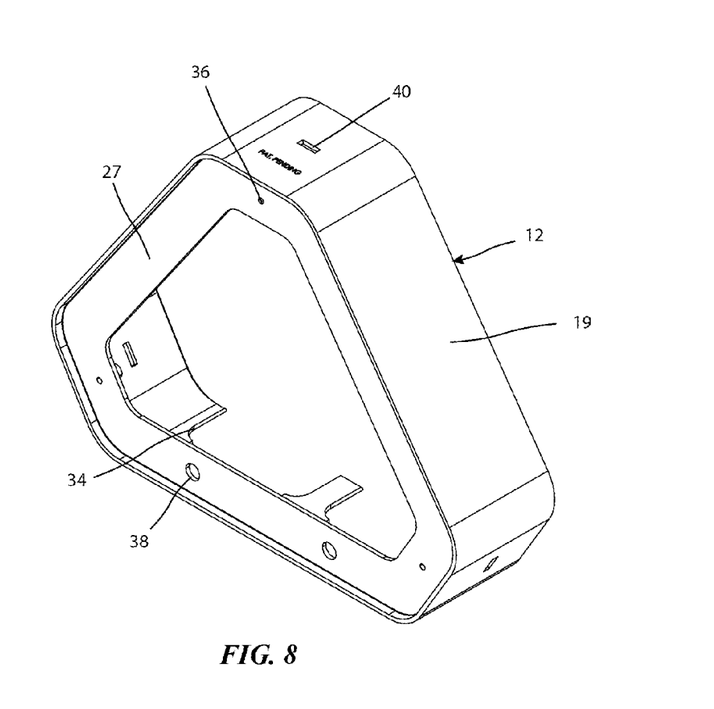
FIG. 8 is an isometric view of the housing of the emergency medicine storage and dispensing device in accordance to one, or more embodiments.
Figure 15:
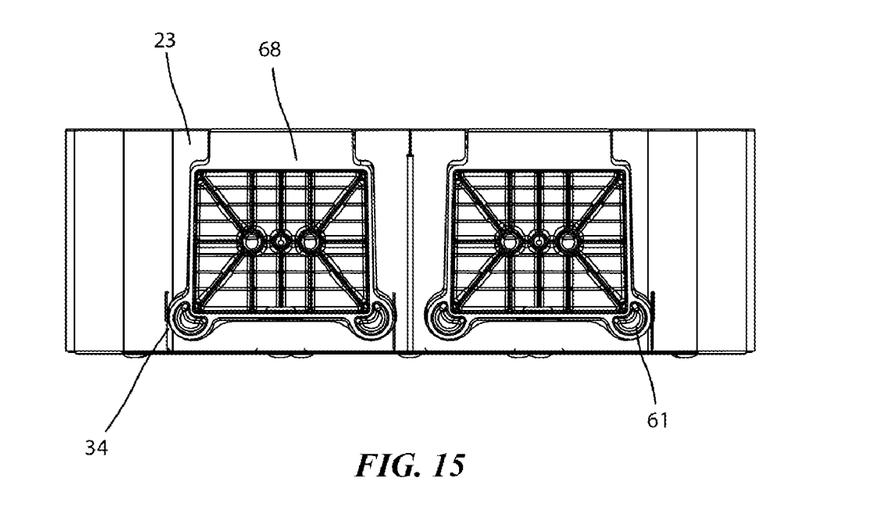
FIG. 15 is a bottom view of yet another embodiment of the emergency medicine storage and dispensing device in accordance to one, or more embodiments.

In embodiments, the back section 16 can have at least one back mounting boss 50 wherein the back mounting boss can align with the cover first hole 26 wherein the at least one housing fastener 28 can couple the front section 14 to the back section 16. The back lip 56 can have at least one back cutout 48 wherein the back cutout can guide the tray 24 up and down into the housing's compartment and back section 16. The back cutout 48 can be such as, for example, a partial circle, square, triangle, rectangle, or the like. The back section 16 can be manufactured from such as, for example, sheet metal, aluminum, plastic, carbon fiber, stainless steel or the like. The tray 24 can be slidably coupled to the at least one cutout 34 and a back cutout 48 that is located on the sidewall 19 and the back lip 56. In certain embodiments the back cutout 48 can be omitted and the tray can slide within the at least one cutout 34 in the front section 14 as shown in FIG. 15. The cutout 34 can be any suitable shape but in the preferred embodiment the cutout can be the same general shape as the tray 60 as shown in FIG. 6 and FIG. 15.

In embodiments, a lip 27 can extend from at least a portion of sidewall 19 to stop the front panel 20 on which the front panel rests when installed. The lip 27 can be partially open allowing the user to see the contents inside of the housing 12 or in other embodiments the lip can be fully enclosed. The lip 27 can have at least one lip first hole 36 wherein the at least one lip first hole can be spaced around the lip evenly or unevenly or on each corner of the lip. The front panel 20 can be place onto the lip 27 and can be clamped between the lip and a cover 18. The cover 18 can have at least one cover first hole 26 and the front panel 20 can have at least one front panel hole 24 in the same location as the lip first hole 36 on the lip 27 wherein the at least one housing fastener 28 can be placed through the cover, front panel, and lip first hole. In certain embodiments the at least one housing fastener 28 can couple the cover 18, front panel 20 and housing 12 to the back section 16 through at least one back mounting boss 50 or in other embodiments can be secured directly to the front section 14. The fasteners 28 can be such as, for example, screw, bolt, pan head, rounded, rivets, flat head, shoulder, socket head, or the like.

Figure 16:
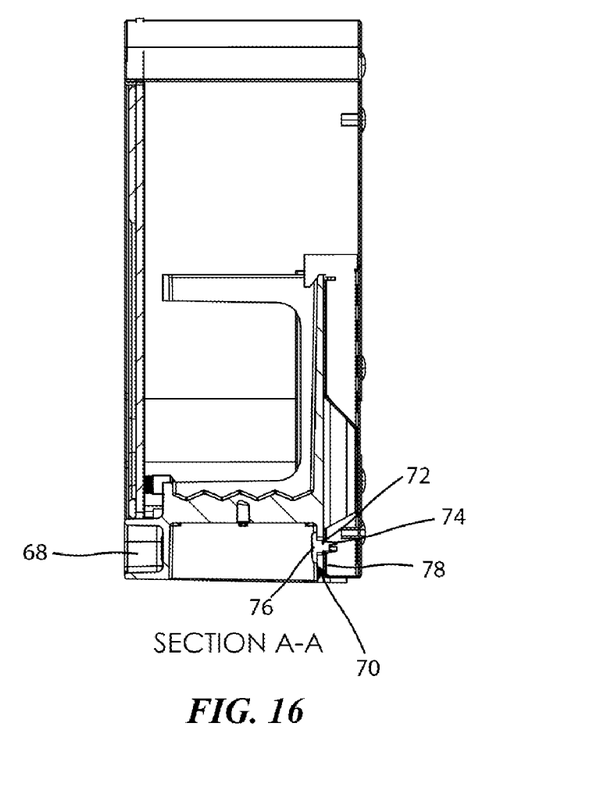
FIG. 16 is a cross section view of FIG. 13 section A-A of yet another embodiment of the emergency medicine storage and dispensing device in accordance to one, or more embodiments.

The cover 18 can secure the front panel 20 between the lip 27 and the front edge 21 when the cover is installed to the housing 12, the cover can have at least one cover pinhole 29 that aligns with the front panel pinhole 25 and a lip pinhole 38. The lip pinhole 38 can be located substantially near the bottom of the lip 27 or in other embodiments the lip pinhole can be positioned on a pinhole tab 78 as shown in FIG. 16. The front panel 20 can be clear or solid and can be manufactured from such as, for example, glass, plastic, plexiglass, polycarbonate, laminated glass or the like.

Figure 1:
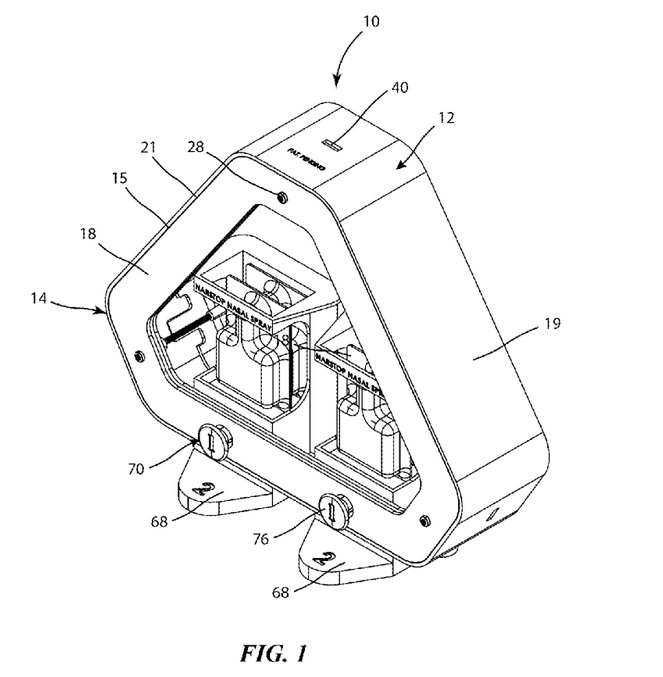
FIG. 1 is an isometric view of the emergency medicine storage and dispensing device in accordance to one, or more embodiments.

In embodiments, the housing 12 including the front section 14, the back section 16, the cover 18, and the front panel 20 can be substantially the same shape wherein the shape can be such as for example, is triangular with chamfered ends, circular, square, rectangular, hexagon, octagonal or the like, the preferred embodiment is as shown in FIG. 1. The cover 18 can be colored a bright color such as, for example, orange, yellow, red, or the like. The cover 18 can be manufactured from such as, for example, sheet metal, aluminum, plastic, carbon fiber, stainless steel, sheet metal or the like.

In embodiments, the tray 60 can have a tray body 62 with at least one tray slot 63 extending from the body to a tray retainer 64 wherein the tray slot can extend up through the tray retainer. The tray 60 can have a tray pinhole 66 that aligns with the cover pinhole 29 and the front panel pinhole 25 when the tray is position in the housing 12. In certain embodiments, the tray pinhole can be positioned on the underside of the tray and can align with the hole on the pinhole tab 78 as shown in FIG. 16. In embodiments, the tray retainer 64 can extend beyond the tray body 62 and the tray slot 58 wherein the tray retainer can retain the tray in the housing 12 while in its open position giving the user access only to the contents within the tray slot 58. The tray 24 can have at least one guide 60 that extends from the tray body 62 to the tray slot 58.

Figure 2:
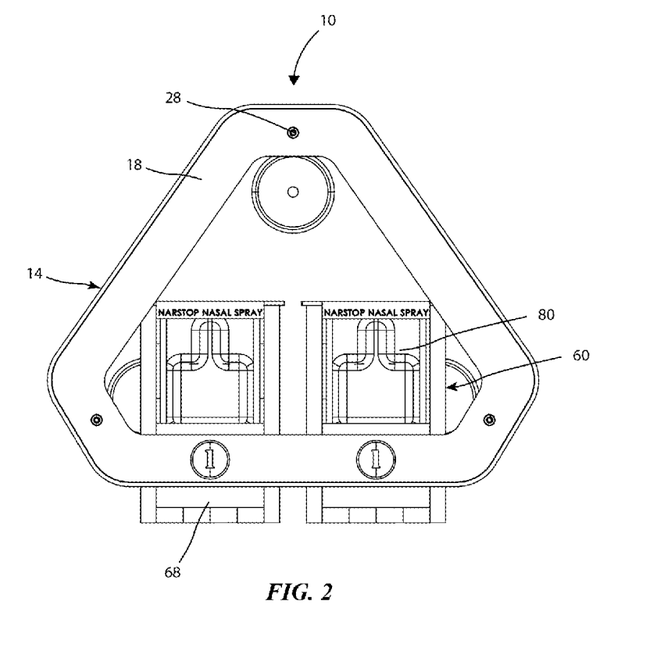
FIG. 2 is a front view of the emergency medicine storage and dispensing device in accordance to one, or more embodiments.
Figure 3:
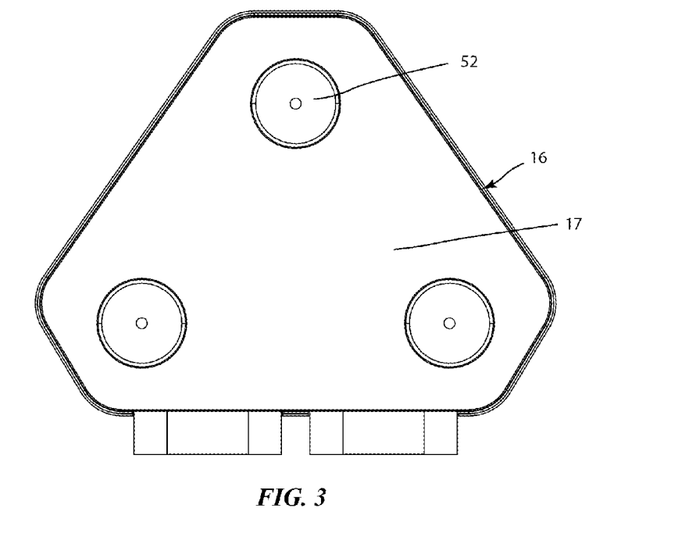
FIG. 3 is a back view of the emergency medicine storage and dispensing device in accordance to one, or more embodiments.
Figure 4:
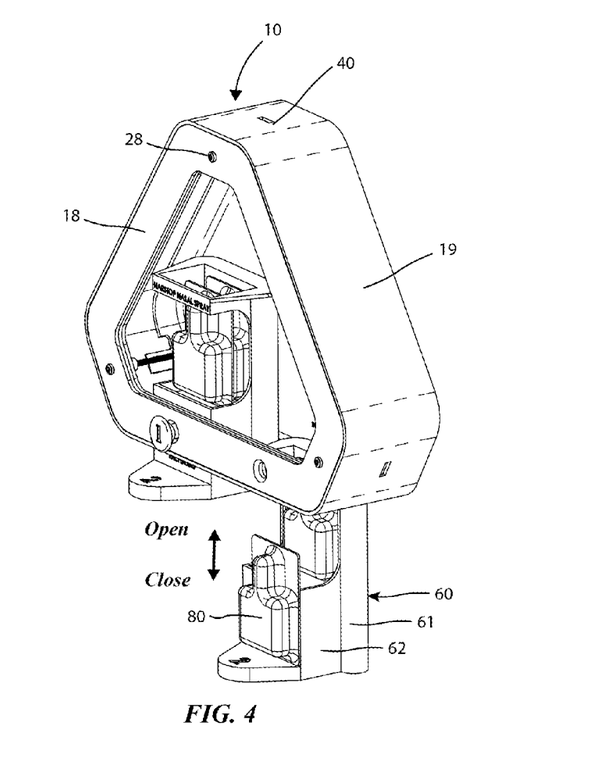
FIG. 4 is an isometric view of the emergency medicine storage and dispensing device in its open position with the pin released in accordance to one, or more embodiments.
Figure 5:
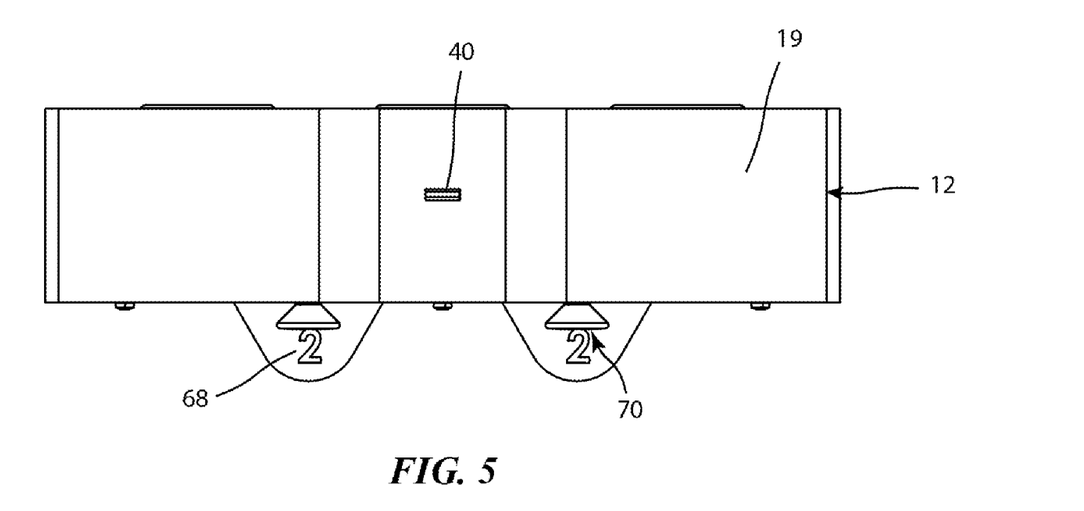
FIG. 5 is a top view of the emergency medicine storage and dispensing device in accordance to one, or more embodiments.
Figure 10:
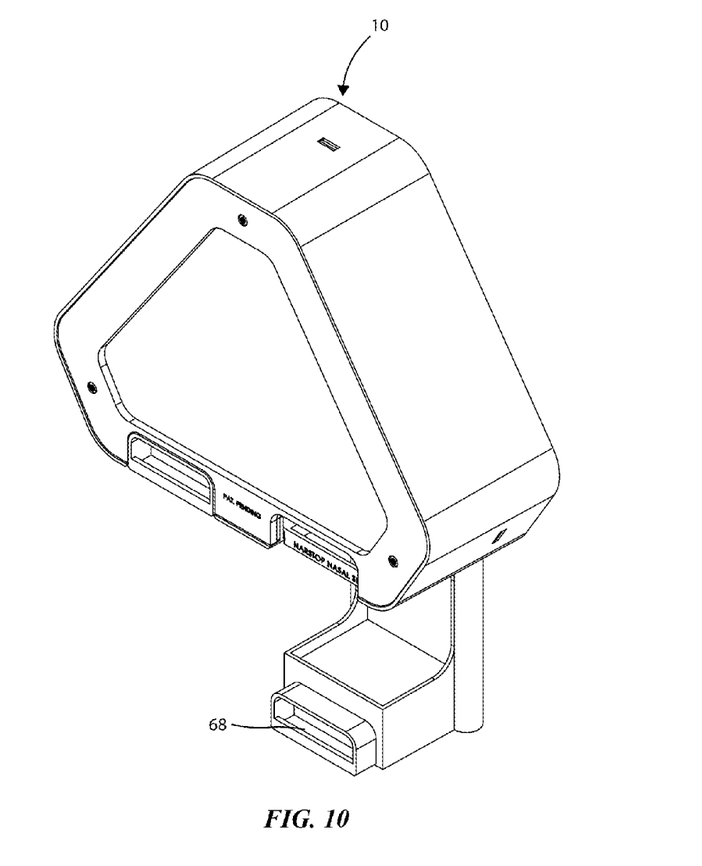
FIG. 10 is an isometric view of another embodiment of the emergency medicine storage and dispensing device in accordance to one, or more embodiments.
Figure 13:
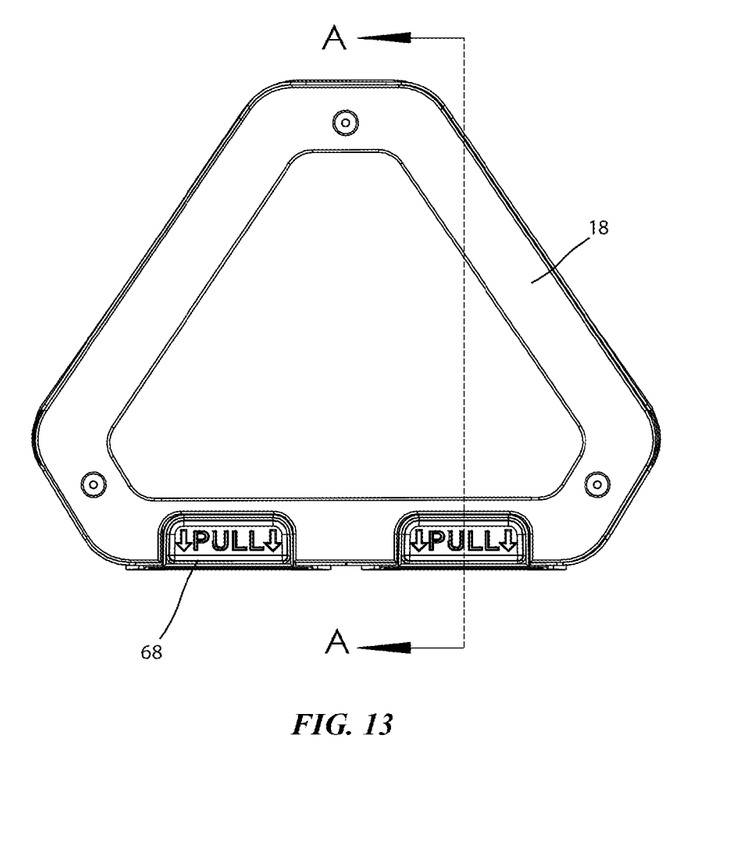
FIG. 13 is a front view of yet another embodiment of the emergency medicine storage and dispensing device in accordance to one, or more embodiments.

A tray 24 configured to slide into the housing 12 through the at least one cutout 34, the tray having a tray pinhole 66 that aligns with the cover pinhole 29 and the front panel pinhole 25 when the tray is slid into the housing 12. The tray body 62 can have at least one tray pinhole 66 located on its frontside, bottom side or back side. The tray 60 can be retained in its closed position by at least one pin 70 that can engage the tray pinhole 66 with a slot while within the chamber of the housing 12 and/or the back section 16 that is located on either front of the tray body 62 or the back of tray body and/or on the back section 16. The tray 60 can have a handle 68 located on the tray body 62 wherein the handle can extend past the housing 12 or can be flush with the housing or recessed from the housing which can allow the user easy access to pull down on the tray as shown in FIG. 2, 10 or 13. The tray 70 can be manufactured from such as, for example, plastic, metal, carbon, or the like and formed by such as, for example, machined, molded, casted, forged, or the like.

In embodiments, the pin 70 can secure the tray 24 in the housing 12. The pin 70 can be a break away pin having a thin break away section 72 and a capturing section 74. The pin 70 can have a breakaway section 72 that is between a pin head 76 and a capture section 74 wherein the breakaway section can break when the user pulls on the pin dropping the tray 24 revealing at least one rapid chemical deployment system 80 within the tray. The breakaway section can be thinner than the pin end and can retain the tray within the housing's chamber. The pin 70 can be manufactured from such as, for example, plastic, metal, carbon, or the like. The at least one rapid chemical deployment system 80 is an opioid overdose reversal medicine.

Figure 9:
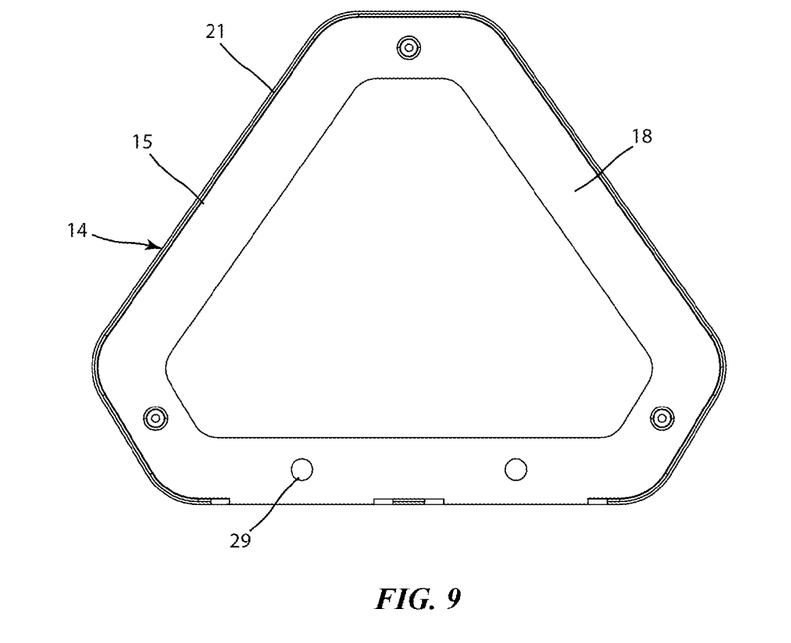
FIG. 9 is a front view of another embodiment of the emergency medicine storage and dispensing device in accordance to one, or more embodiments.
Figure 11:
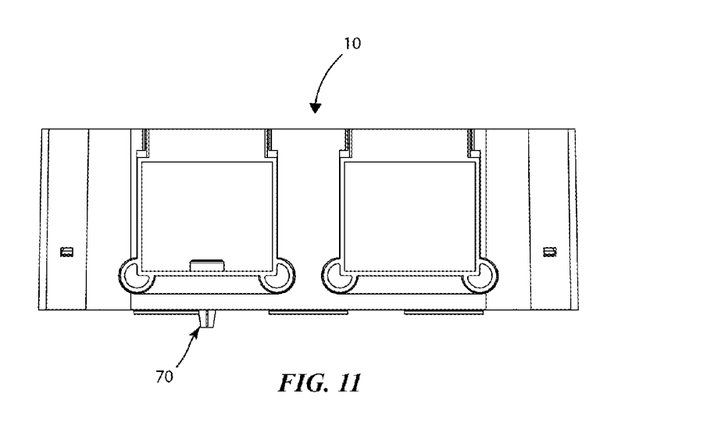
FIG. 11 is a bottom view of another embodiment in its open position of the emergency medicine storage and dispensing device in accordance to one, or more embodiments.
Figure 12:
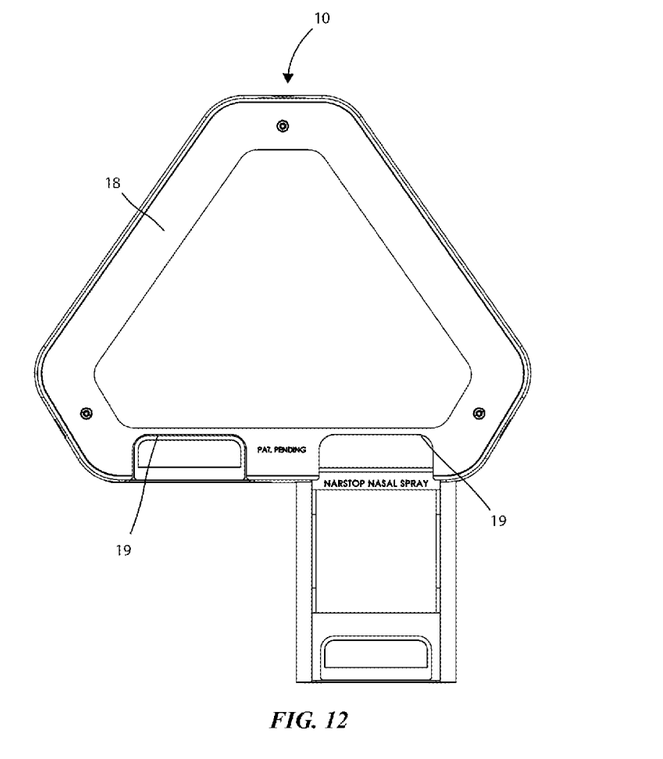
FIG. 12 is a front view of another embodiment with a tray in its open position of the emergency medicine storage and dispensing device in accordance to one, or more embodiments.

In certain embodiments as shown in FIG. 9-11, the housing 12, the cover 18, and the front panel 20 can have at least one cutout 34 to allow for a tray handle 68 to sit partially flush or flush with the bottom of the housing wherein the handle 68 can protrude from the tray body allowing the user to pull down on the tray. The pin 70 can be on located on the tray body and can extend through the housing 12, wherein the pin can break away or can be pulled out to allow the tray 24 to drop down and allow the user access to its contents.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only and is not intended to limit the scope of the present disclosure, which is defined solely by the claims. Accordingly, embodiments of the present disclosure are not limited to those precisely as shown and described.

Certain embodiments are described herein, including the best mode known to the inventors for carrying out the methods and devices described herein. Of course, variations on these described embodiments will become apparent to those of ordinary skill in the art upon reading the foregoing description. Accordingly, this disclosure includes all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

What is claimed is:

1. An emergency medicine storage and dispensing device comprising:
    a housing comprising a front section and a back section detachably coupled to the front section, the front and back sections when assembled defining a front having a front edge, a back, and a sidewall about the periphery of the housing between the front and the back of the housing;
    wherein the front has a cross section and the sidewall has a bottom side;
    wherein the front section comprises a front panel that resides within the sidewall of the front section and encloses the front of the housing, the front panel having at least one front panel pinhole;
    a lip that extends from at least a portion of sidewall to stop the front panel and on which the front panel rests when installed;
    a cover that secures the front panel between the lip and the front edge when the cover is installed to the housing, the cover having at least one cover pinhole that aligns with the at least one front panel pinhole;
    at least one cutout in the bottom side of the sidewall;
    a tray configured to slide into the housing through the at least one cutout; and
    a pin that secures the tray in the housing.

2. The emergency medicine storage and dispensing device according to claim 1, wherein the front panel is at least partially transparent and manufactured from one of glass, plastic, plexiglass, polycarbonate, and laminated glass.

3. The emergency medicine storage and dispensing device according to claim 1, wherein the pin is a break away pin having a thin break away section and a capturing section.

4. The emergency medicine storage and dispensing device according to claim 1, wherein the front panel is compressed against the housing by at least one fastener.

5. The emergency medicine storage and dispensing device according to claim 1, wherein the back section has at least one wall mounting hole.

6. The emergency medicine storage and dispensing device according to claim 5, wherein the back cover has at least one snap hook and at least one mounting boss.

7. The emergency medicine storage and dispensing device according to claim 6, wherein the at least one housing fastener is attached to the at least one mounting boss.

8. The emergency medicine storage and dispensing device according to claim 7, wherein the front section is coupled to the back section by the at least one housing fastener or by at least one back flange and at least one back fastener.

9. The emergency medicine storage and dispensing device according to claim 7, wherein the housing fastener is one of a rivet, snap hook, and bolt.

10. The emergency medicine storage and dispensing device according to claim 6, wherein the front section, back section, cover, and front panel are substantially the same shape wherein the shape is triangular with chamfered ends.

11. The emergency medicine storage and dispensing device according to claim 6, wherein the back section comprises at least one back cutout.

12. The emergency medicine storage and dispensing device according to claim 1, wherein the tray has at least one slot that holds at least one rapid chemical deployment system.

13. The emergency medicine storage and dispensing device according to claim 12, wherein the at least one rapid chemical deployment system is an opioid overdose reversal medicine.

14. The emergency medicine storage and dispensing device according to claim 1, wherein the at least one tray has a retainer that keeps the tray from being completely removed from the housing.

15. The emergency medicine storage and dispensing device according to claim 1, wherein the tray has a handle.

16. The emergency medicine storage and dispensing device according to claim 1, wherein the tray has a tray pinhole that aligns with the at least one cover pinhole and the at least one front panel pinhole when the tray is slid into the housing or to a pinhole flange.

* * * * *